(12) United States Patent
Gagliano et al.

(10) Patent No.: US 6,932,608 B1
(45) Date of Patent: Aug. 23, 2005

(54) TWO-PIECE MODEL AND DIE SYSTEM

(75) Inventors: James Salvatore Gagliano, Tampa, FL (US); Gavin Atlas Steele, IV, White Heath, IL (US)

(73) Assignee: GBase, Inc., Tampa, FL (US)

( * ) Notice: Subject to any disclaimer, the term of this patent is extended or adjusted under 35 U.S.C. 154(b) by 62 days.

(21) Appl. No.: 10/249,945

(22) Filed: May 21, 2003

(51) Int. Cl.[7] .................................................. A61C 11/00
(52) U.S. Cl. ......................... 433/213; 433/60; 433/74
(58) Field of Search ............................ 433/213, 60, 74, 433/24

(56) References Cited

U.S. PATENT DOCUMENTS

| | | | |
|---|---|---|---|
| 4,122,606 A | 10/1978 | Roman | |
| 4,203,219 A | 5/1980 | Wiener | |
| 4,265,619 A | 5/1981 | Lucki et al. | |
| 4,371,339 A | 2/1983 | Zeiser | |
| 4,398,884 A | 8/1983 | Huffman | |
| 4,412,822 A * | 11/1983 | Blechner | 433/60 |
| 4,521,188 A | 6/1985 | Metzler | |
| 4,708,835 A | 11/1987 | Kiefer | |
| 4,898,359 A | 2/1990 | Gopon | |
| 5,197,874 A | 3/1993 | Silva et al. | |
| 5,393,227 A | 2/1995 | Nooning | |
| 5,466,152 A | 11/1995 | Walter | |
| 5,775,899 A | 7/1998 | Huffman | |
| 5,788,489 A * | 8/1998 | Huffman | 433/60 |
| 6,217,326 B1 | 4/2001 | Hahn | |
| 6,227,851 B1 | 5/2001 | Chishti et al. | |

* cited by examiner

*Primary Examiner*—Cary E. O'Connor
*Assistant Examiner*—Candice C. Stokes
(74) *Attorney, Agent, or Firm*—Smith & Hopen, P.A.; Ronald E. Smith

(57) ABSTRACT

A model and die system has a working quadrant of parallelepiped construction and a opposing quadrant of the same construction. The working quadrant has an upper flat surface disposed in confronting relation to a lower flat surface of the opposing quadrant. Pin-receiving bores are formed in the working quadrant and mounting members depend from the opposing quadrant. Each cast tooth supported by the working quadrant has a pin depending from it and is fully seatable against the upper flat surface. Each cast tooth mounted on the upper flat surface is secured to a mounting post that depends from the upper flat surface. In a first embodiment, the quadrants are held in spaced apart, adjustable vertical relation to one another by a pair of parallel guideposts. In a second embodiment, an articulated hinge performs that function. In a third embodiment, a semicircular base opposes a semicircular top member.

12 Claims, 5 Drawing Sheets

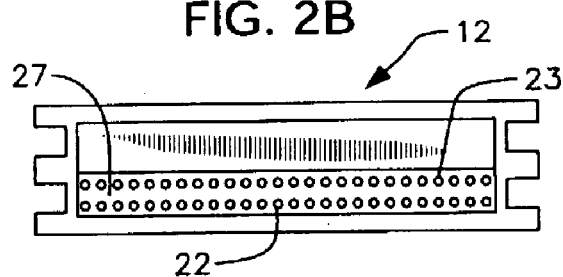
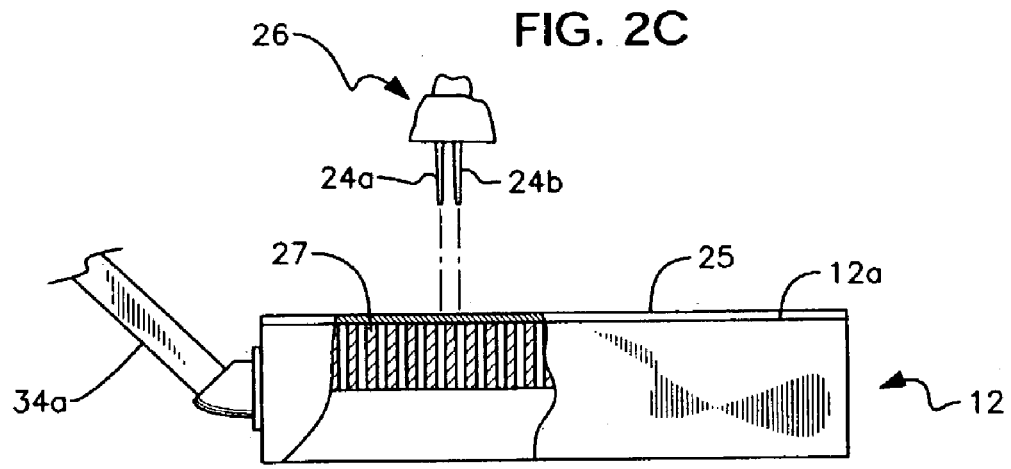
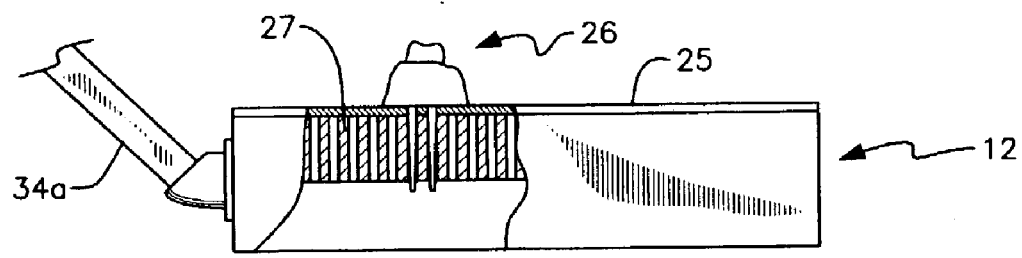

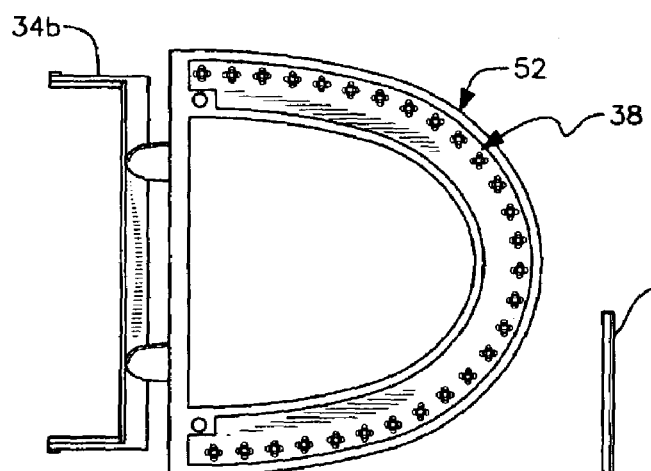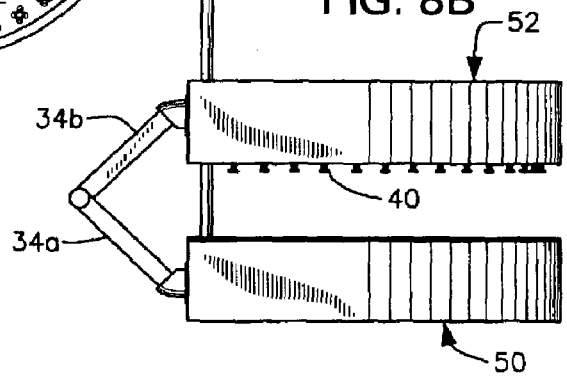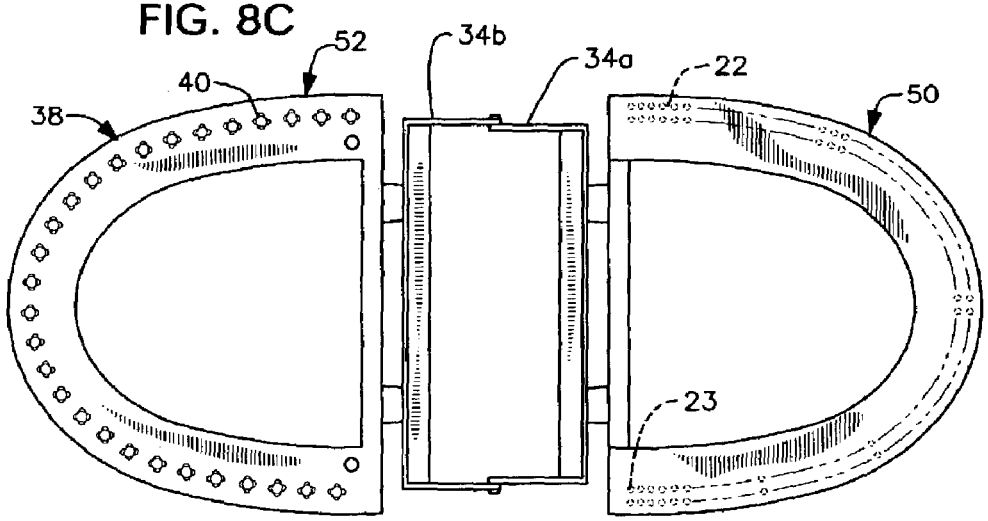

TWO-PIECE MODEL AND DIE SYSTEM

BACKGROUND OF INVENTION

1. Field of the Invention

This invention relates, generally, to dentistry. More particularly, it relates to a model and die system for making casts of dental impressions for the shaping of crowns and dentures.

2. Description of the Prior Art

The use of triple trays is now the most common technique for taking impressions. Also known as dual-arch trays, they capture the area to be restored, the opposing area, and the bite relationship. Errors can arise, however, when a bite registration is transferred from a triple tray impression to an articulation hinge such as a Vertex®, Orbiz®, Quickulator®), or to a generic metal articulation hinge.

The current method for transferring a bite registration from a triple tray to an articulation hinge includes the initial step of mixing dental stone powder to make a batch of liquid dental stone and pouring the liquid dental stone into the impression on the prep side first. The stone is allowed to cure for about thirty (30) minutes. Another batch of liquid stone is then poured into the opposing side of the impression and allowed to cure for about thirty (30) minutes at which time the model of the teeth is removed.

The model with the prepared teeth is then ground on a model trimmer. The bottom of the model must be completely flat all the way across. A router or a hand piece and burr are then used to bevel the model edges. The model is then dried and cleaned.

Holes are then drilled in the bottom of the model in registration with the preps and other sections of the working model. The model is then cleaned again.

Next, dowel pins are glued into the holes. Typically, there are two dowel pins for each section. The glue is allowed to set and dry. A separating agent is then sprayed onto the bottom of the model. After the separating agent has dried at least slightly, a batch of working quadrant stone is then prepared and poured into a working quadrant former. Model pins are then inserted into the working quadrant former. The working quadrant stone is allowed to set in accordance with the manufacturer's suggested time, which is usually around thirty (30) minutes. The model teeth are then removed from the working quadrant with the pins exposed. The bottom of the working quadrant is ground to expose the die pinholes. The holes are then cleaned of debris and the model is cut into sections using a hand piece and disc or a die saw. The dowel pins are then cleaned because the separating medium leaves a film on the dowel pins that can hinder the die section and other sections of the model from seating down all the way in the working quadrant. The crown or denture being prepared will not fit the patient if the sections and dies do not seat all the way flat into the working quadrant stone.

The opposing arch is then removed from the impression. It is trimmed on a model trimmer and placed in a working quadrant former. A batch of stone is mixed and poured into the working quadrant former to hold the opposing arch. After the stone has set for about thirty (30) minutes, the technician then articulates both arches.

Articulation is currently performed by hand and eye to try and "guess" where the correct centric bite is located. A hinge is then glued into place to maintain the bite that has been deemed to be the correct bite. This completes the working model and the case is ready to proceed with fabrication of the restoration.

This method is very labor-intensive and mistakes at any step can result in a substandard working model. For example, it is difficult to always achieve the optimal water and powder ratio to produce the working quadrant stone. Further steps that are difficult to optimize include the grinding of the model, the placement and gluing of the dowel pins, and the articulation of the models to produce proper occlusion in the mouth. Further difficulties include breaking the model during drilling or trimming of holes which necessitates re-starting the process from the beginning, and the optimization of many other variables not expressly mentioned herein but well-known to those who work in this field.

Several techniques have been developed in an effort to improve the above-described process. Some technicians, for example, have developed their own articulation hinges in an attempt to avoid use of the above-mentioned commercially available articulation hinges. Moreover, the model has been placed in the center of the tray but this technique has the disadvantage of making the prep hard to reach and hard to see.

Most of the known systems prevent the technician from determining whether or not the dies are completely seated. Moreover, in all of the known systems it is difficult to put in and take out the dies from the working quadrant. Most known systems do not provide good centric opposing quadrants for occlusion nor do they provide a free and centric opposing quadrant. Nor does any known system employ double dowel pins to stabilize dies.

What is needed, then, is a system that is much less labor intensive than the known systems. The needed system would reduce the amount of guesswork, artistry, and skill required under the known systems. It would therefore standardize the procedure and enable a technician to work with ease and accuracy. The resulting models would be superior to the models made under the current system.

More particularly, an optimal system would enable a technician to use any of the commercially-available articulation hinges. In an optimal system, the dies would always be placed in a labial position so that they would be easy to reach and see. An optimal system would provide a flat working quadrant with no obstructions so that it can be determined whether or not the dies are properly seated. Each die and model section should be double dowel-pinned and each die should have an exact, easy path of insertion. Movement should always be solid, never centric. The improved system should also provide a complete mesial or distal centric opposing quadrant.

U.S. Pat. No. 4,382,787 to Huffman discloses a dental model articulator for mounting and holding dental model casts necessary for the correction or alteration of teeth. The articulator includes two mirror-image brackets, connected together through a hinging mechanism, that are attached to a mounting means. Huffman further discloses a mechanism including a working quadrant with an opposing element for securing dental molds. This ensures that the bite between the lower and upper casts is optimal. Huffman does not include pin-receiving bores in a working quadrant nor does Huffman disclose elevated mounting members located in an opposing quadrant.

U.S. Pat. No. 6,471,513, also to Huffman, discloses a dental model working quadrant assembly having preformed apertures for securing or reconstructing a dental model. The supporting working quadrant includes apertures situated in two rows located between indexing studs. Two rows of apertures are contained in the support structure, with the external aperture row being offset from and adjacent to the internal aperture row. These apertures are designed to receive tapered pins. The working quadrant may be attached to an articulator either through an articulator plate or through the use of a latch and a slot located on the mounting working quadrant.

A mechanism with lower and upper support means that produces a more accurate recreation of restorative work is disclosed in U.S. Pat. No. 5,466,152 to Walter. The support means is connected at one end through the use of an anti-rotational guide located at a hinged end. A plurality of indexing holes are situated throughout the surface of the support member. The dental model is affixed to the support member through the attachment of indexing pins corresponding to predetermined indexing holes. A hinge and indexing pins stabilize the support working quadrant and opposing structure and thus produce a fairly accurate representation of a dental restoration model. There are no offset, preformed bores that enables the efficient trimming of excess casting material.

In view of the prior art considered as a whole at the time the present invention was made, it was not obvious to those of ordinary skill in the pertinent art how the current systems could be improved.

SUMMARY OF INVENTION

The long-standing but heretofore unfulfilled need for improvements in die and model systems is now met by a new, useful, and nonobvious invention.

In a first embodiment of this invention, the novel model and die system includes a base, known in the industry as a working quadrant, of generally straight, parallelepiped construction having a flat upper surface. The system further includes a top member, known in the industry as an opposing quadrant, of generally straight, parallelepiped construction having a flat lower surface. The working quadrant and the opposing quadrant are disposed in vertically spaced apart registration with one another. The working quadrant and the opposing quadrant have a common predetermined longitudinal extent, a common predetermined transverse extent, and a common predetermined height.

In the first embodiment, a pair of upstanding guideposts is mounted to the working quadrant, there being one guidepost at each end of the working quadrant. A pair of guidepost-receiving throughbores is formed in opposite ends of the opposing quadrant. Each guidepost of the pair of guideposts is slideably received within an associated throughbore so that the space between the working quadrant and opposing quadrant is adjustable by sliding the opposing quadrant along the length of the upstanding guideposts. The guideposts also maintain the vertically spaced apart registration between the working quadrant and opposing quadrant as the opposing quadrant is displaced.

The working quadrant is solid beneath part of the flat upper surface. A first row of bores is formed in the working quadrant in closely spaced apart relation to a preselected longitudinally extending edge of the working quadrant. A second row of bores is formed in the working quadrant in parallel relation to the first row of apertures. The second row of bores is spaced further from said preselected longitudinally extending edge than is said first row of bores, i.e., said first row of bores is spaced between said second row of bores and said longitudinally extending edge.

The working quadrant is hollow beneath that part of the flat upper surface where no bores are formed. Each bore is adapted to receive a pin that depends from a cast tooth and gum segment. Thus, the solid part beneath the flat upper surface has a depth sufficient to receive a pin but said depth may be less than the height of the sidewalls of the working quadrant.

A thin metallic foil overlies the flat upper surface of the working quadrant so that dental stone does not flow from bores that are not in use, as will become more clear as this description proceeds.

Each cast tooth of a plurality of cast teeth supported by the working quadrant has a pair of pins depending from it. Moreover, a pair of cast teeth, or perhaps a group of three teeth, may be formed as a unit and each unit has a pair of pins depending therefrom. Each pin is snugly received within a preselected bore of the plurality of bores formed in the working quadrant. More specifically, each pair of pins includes a first pin that is received with a bore of the first row of bores and a second pin that is received within a bore of the second row of bores. A pin punctures the foil mentioned above when a cast tooth is mounted on the working quadrant in a manner disclosed hereinafter.

At least one cast tooth having a pair of pins depending therefrom and snugly received within associated bores of said first and second rows of bores formed in the working quadrant is positioned so that a leading surface of the at least one cast tooth is substantially flush with the preselected leading edge of the working quadrant. This minimizes trimming of excess materials.

The opposing quadrant is an essentially hollow structure, including a flat lower surface and sidewalls projecting upwardly from a periphery thereof. A plurality of apertures is formed in the flat lower surface. The plurality of apertures includes a plurality of sets of apertures where the sets of apertures are arranged in a longitudinally-extending row. More particularly, four apertures arranged in circumferentially spaced relation to one another collectively form one set of apertures. In a commercial embodiment of the invention, there are ten (10) sets of said apertures.

A mounting member in the form of a mounting post is associated with each set of apertures so that in said commercial embodiment there are ten (10) of said mounting posts. Each mounting post is centered with respect to its associated set of apertures, each mounting post is fluted, and each mounting post depends from the lower flat surface of the working quadrant.

Each mounting post has four semicircular flutes, each of which is in registration with an associated aperture and the depth of each flute is substantially equal to the radius of its associated aperture. In this way, no part of the mounting post occludes any of its four associated apertures.

The flutes extend from the flat lower surface to a point about two-thirds of the extent of each mounting post. Accordingly, about the lower third of each mounting post is not fluted, thereby forming a disc-shaped head at the bottom of each mounting post. Thus, there is an undercut formed in each post where a flute meets the head.

In the commercial embodiment where each set of apertures has four apertures and where each post has four flutes, the number of undercuts in each post is four. The number of apertures and hence the number of flutes and hence the number of undercuts may be increased or decreased. Four (4) is merely considered to be an optimal number but other numbers of apertures per set of apertures and hence other numbers of flutes and undercuts are within the scope of this invention.

This arrangement of sets of apertures where each set of apertures has a mounting post associated with it and where each mounting post is fluted as described and surmounted by an unfluted head to create a plurality of undercuts is provided to hold the cast teeth that depend from the lower flat surface of the opposing quadrant. The dental stone used to make the gums associated with the cast teeth fills the apertures and the flutes. The respective heads of the posts support the dental stone because the posts depend from said flat lower surface.

Thus, there are no pins associated with the cast teeth that depend from the opposing quadrant. It should be understood that if the opposing quadrant were provided with the pin-receiving bores of the working quadrant, any pins placed into said bores would fall out under the influence of gravity. The fluted posts that depend from the lower surface of the opposing quadrant are secured to the flat lower surface and cannot separate therefrom. Accordingly, when dental stone hardens in said flutes and undercuts, the cast gums and teeth associated with the opposing quadrant cannot fall under the influence of gravity after the dental stone has cured.

In the first embodiment, a bite between the at least one cast tooth mounted to the working quadrant and the at least one cast tooth mounted to the opposing quadrant is checked by sliding the opposing quadrant toward the working quadrant until the cast teeth abut one another.

In a second embodiment, the guideposts of the first embodiment are eliminated and the quadrants are interconnected to one another by a hinge.

In a third embodiment, the working quadrant has a semicircular configuration and therefore represents an entire set of lower teeth, not just a quadrant thereof. It is therefore referred to as the working base. Similarly, the opposing quadrant has a semicircular configuration and therefore represents an entire set of upper teeth, not just a quadrant thereof. It is therefore referred to as the opposing top member. However, in all other respects, the semicircular working base has the same structure as the straight working quadrant and the semicircular opposing top member has the same structure as the straight opposing quadrant.

An important object of this invention is to provide an improved model and die system that lowers the level of skill required to produce a good set of model teeth.

A closely related object is to provide an improved system that substantially reduces the time required to produce a good set of model teeth.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 2B is a bottom plan view of the working quadrant;

FIG. 2C is a side elevational, partially cut-away view of the working quadrant depicting a cast tooth spaced apart therefrom;

FIG. 2D is a side elevational, partially cut-away view of the working quadrant depicting the cast tooth of FIG. 2C in its engaged configuration;

FIG. 8A is a top plan view of a third embodiment;

FIG. 8B is a side elevational view of the third embodiment; and

FIG. 8C is a top plan view of said third embodiment when unfolded.

DETAILED DESCRIPTION

Figure 1:
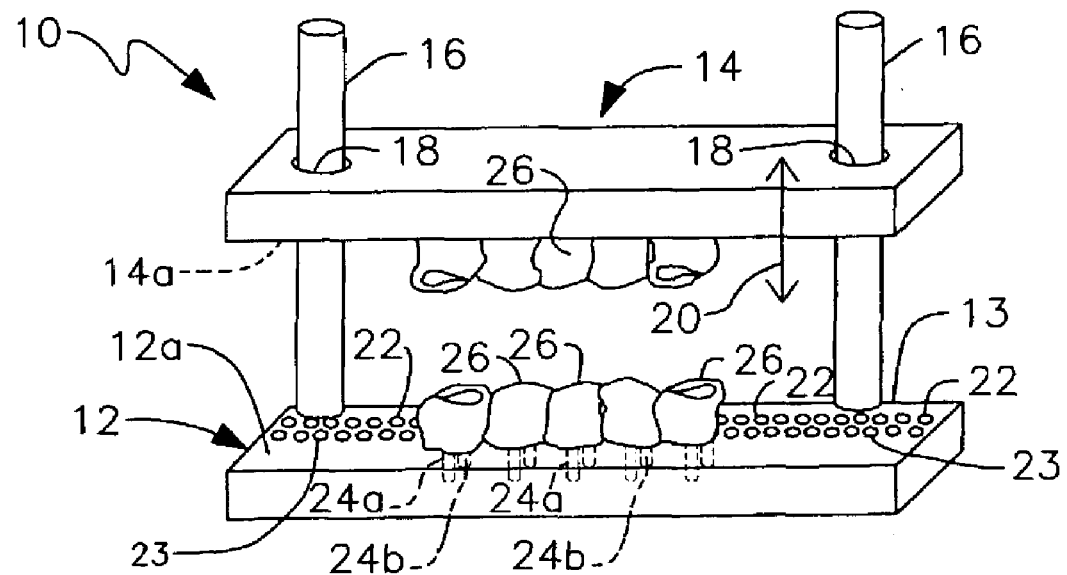
FIG. 1 is a diagrammatic view of the first embodiment.

Referring to FIG. 1, it will there be seen that the reference numeral 10 denotes an illustrative embodiment of the present invention as a whole.

The first embodiment of novel system 10 includes a working base or quadrant 12 and an opposing top member or opposing quadrant 14 having essentially the same structure as working quadrant 12. More particularly, working quadrant 12 and opposing quadrant 14 share a generally straight, parallelepiped configuration having a predetermined length, width, and height.

Working quadrant 12 has a flat upper surface 12a and opposing quadrant 14 has a flat lower surface 14a. Flat upper surface 12a is disposed in confronting relation to lower flat surface 14a.

In a first embodiment, a pair of upstanding guideposts, collectively denoted 16, interconnects working quadrant 12 and opposing quadrant 14. The respective lowermost ends of guideposts 16 are secured to working quadrant 12 by any suitable means, near opposite ends thereof. Two longitudinally spaced apart throughbores 18 are formed in opposing quadrant 14 to slidingly receive said posts so that opposing quadrant 14 may be easily moved toward or away from working quadrant 12 as indicated by double-headed directional arrow 20.

Posts 16, 16 are snugly received within their respective bores 18, 18 so that friction maintains opposing quadrant 14 in any position of functional adjustment along the length of posts 16, 16. Moving opposing quadrant 14 therefore requires the application of manual force to said opposing quadrant.

A first row of bores, where each bore is denoted 22, is formed in working quadrant 12 in closely spaced apart relation to longitudinally-extending leading edge 13 of working quadrant 12. A second row of bores, where each bore is denoted 23, is formed in parallel relation to the first row of bores. The first row of bores is positioned between the second row of bores and said longitudinally-extending edge.

FIG. 1 further depicts a plurality of metal pins, collectively denoted 24a, 24b and a plurality of cast teeth and gums, collectively denoted 26. Each bore 22 is adapted to snugly receive a metal pin 24a and each bore 23 is adapted to snugly receive a metal pin 24b. The provision of two pins prevents each cast tooth and gum or set of cast teeth and gum from rotating.

Upper surface 12a of working quadrant 12 is perfectly flat. It is therefore easy to see if each cast tooth 26 is perfectly seated, i.e., with its pins 24a, 24b fully seated within its associated bores 22, 23, respectively.

Working quadrant 12 is hollow except in the region below bores 22 and 23. As indicated in the more realistic bottom plan view of FIG. 2B, a solid material 27 is provided within which bores 22, 23 are formed. In a preferred embodiment, all parts of the working quadrant, including the material within which the bores are formed, are formed of a high impact plastic. The use of metallic or other materials is also within the scope of this invention.

Figure 2A:
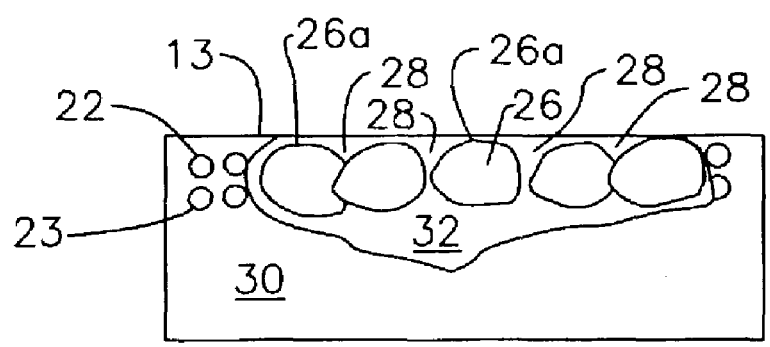
FIG. 2A is a top plan view of a working quadrant of said first embodiment.

As depicted in FIG. 2A, apertures 22 are positioned in offset relation to longitudinally-extending edge 13 of working quadrant 12 as mentioned above so that the forward edge 26a of each cast tooth 26 is substantially flush with said longitudinally-extending edge. This minimizes the amount of trimming that must be performed. In the example of FIG. 2A, the only areas of working quadrant 12 that needs to be trimmed of excess cast material on the labial side of teeth 26 are collectively denoted 28. As further indicated in FIG. 2A, most of working quadrant 12 is removed. The removed area in this particular example is denoted 30. However, a relatively large area, denoted 32, may be left in place because area 32 is hidden from view behind teeth 26 and therefore need not be removed. This saves time and also reduces abrasion to cast teeth 26.

When the excess cast material has been removed, opposing quadrant 14 is simply lowered until cast teeth 26 carried thereby engage cast teeth 26 mounted on working quadrant 12. If the bite is optimal, the upper and lower cast teeth are detached from opposing quadrant 14 and working quadrant 12, respectively, and hinged together using any one of the above-listed commercially available hinge articulators.

Figure 4:
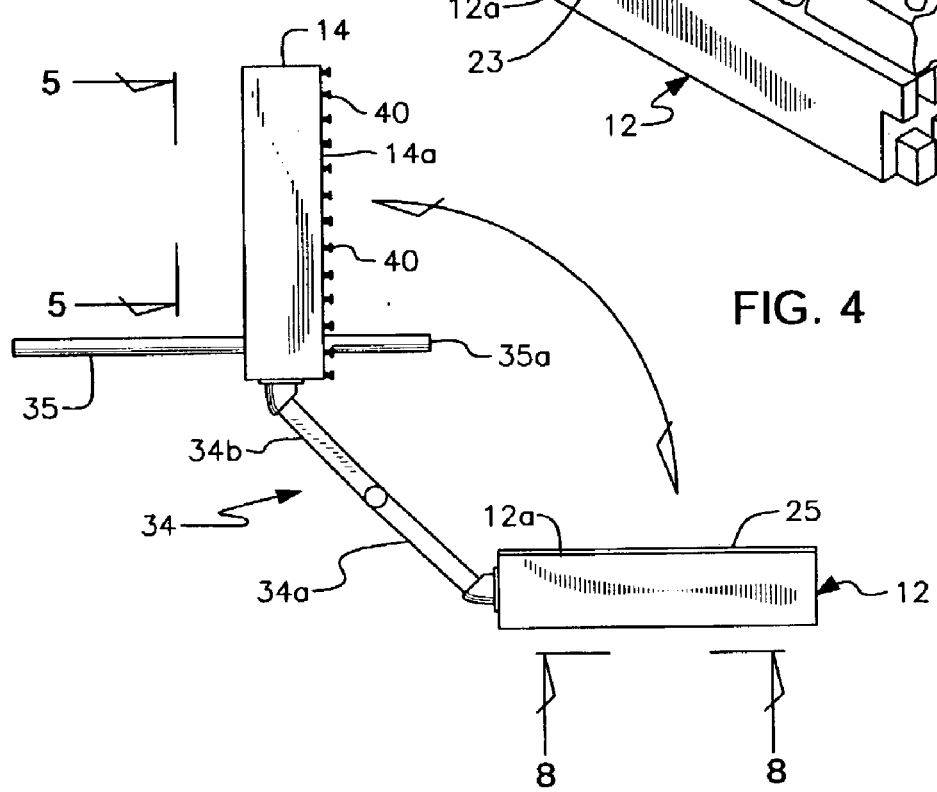
FIG. 4 is a side elevational view of the second embodiment.

A thin metallic film or foil 25, depicted in the more realistic views of FIGS. 2C, 2D, and 4, overlies flat upper surface 12a and covers bores 22, 23. The foil is punctured by pins 24a, 24b when the novel structure is used as perhaps best understood from FIGS. 2C and 2D. Foil 25 prevents dental stone from entering the bores 22, 23 that are not used, i.e., the bores that do not receive pins 24a, 24b remain covered by said foil 25 and thus flat upper surface 12a remains flat. In the absence of foil 25, some of the dental stone could enter into the unused bores and cause bumps or other uneven spots on surface 12a, thus preventing teeth 26 from seating cleanly thereagainst.

There is no corresponding plurality of pin-receiving bores 22, 23 formed in opposing quadrant 14.

FIGS. 3–8C also provide a more realistic view of the novel two-piece model and die system. In those Figures, guideposts 16, 16 of the first embodiment are eliminated and working quadrant 12 is interconnected to opposing quadrant 14 by an articulation hinge 34 (FIGS. 3 and 4) having a first part 34a connected to working quadrant 12 and a second part 34b connected to opposing quadrant 14 as best depicted in FIG. 4. This hinged embodiment is the second embodiment of the invention.

Adjustment rod 35 (FIGS. 3 and 4) is slideably and snugly received within a throughbore formed in opposing quadrant 14. Its flat lowermost end 35a abuts flat upper surface 12a of working quadrant 12 and thus serves as a stop means for hinge 34 when working quadrant 12 and opposing quadrant 14 are disposed in optimal juxtaposition with one another as depicted ion FIG. 3.

It should be understood that quadrants 12 and 14, depicted diagrammatically in FIGS. 1 and 2A in connection with the guidepost embodiment of the invention, actually have the structure as depicted in FIGS. 2B, 2C, 2D, and 3–7. Accordingly, the more detailed description of said quadrants as made hereinafter also applies to the quadrants of FIGS. 1 and 2A.

Figure 3:
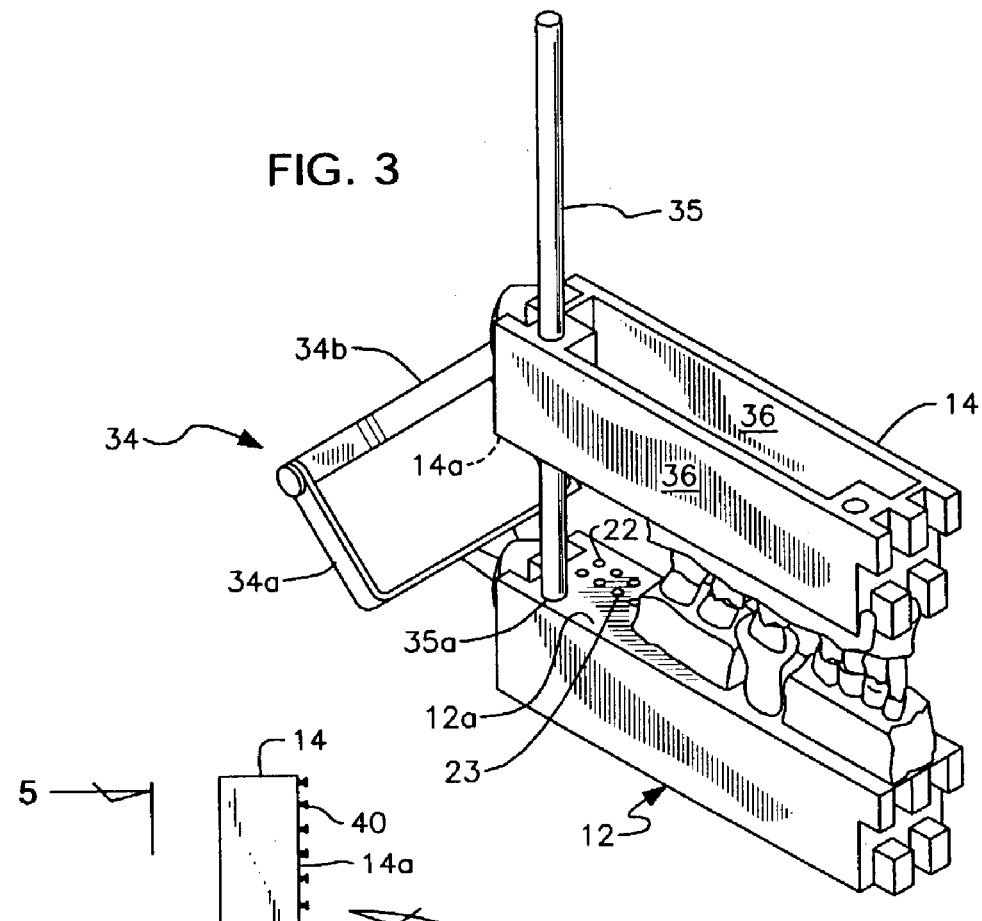
FIG. 3 is a perspective view of a second embodiment.
Figure 5:
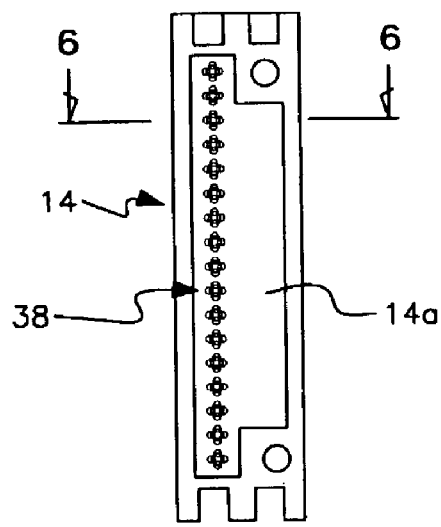
FIG. 5 is a view taken along line 5—5 in FIG. 4.

As best understood in connection with FIG. 3, opposing quadrant 14 is an essentially hollow structure, including the aforesaid flat lower surface 14a and sidewalls 36 projecting upwardly from a periphery thereof. A plurality of sets of apertures is formed in flat lower surface 14a and the sets of apertures are arranged in a row as best depicted in FIG. 5. Each set of apertures is denoted 38 in said FIG. 5. An enlarged view of one set of apertures 38 is provided in FIG. 7.

Figure 7:
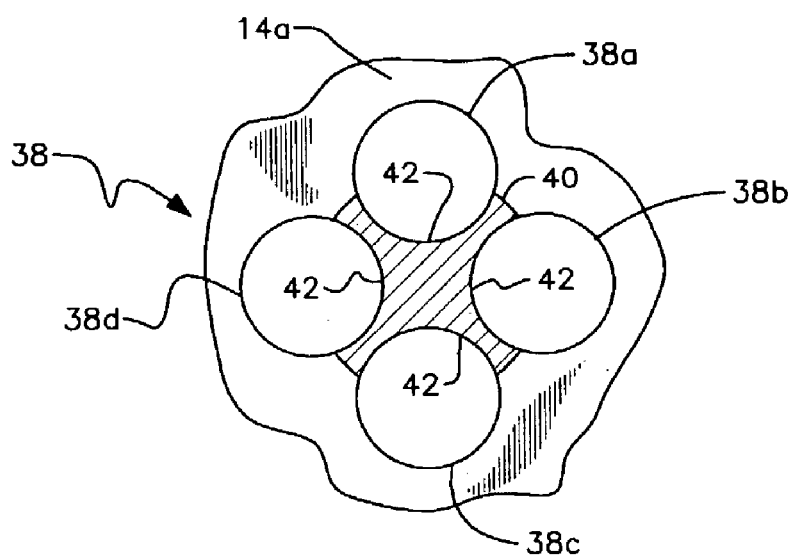
FIG. 7 is a sectional, enlarged view taken along line 7—7 in FIG. 6.

More particularly, as best depicted in said FIG. 7, four apertures 38a, 38b, 38c, and 38d arranged in circumferentially spaced relation to one another collectively form one set of apertures. In a commercial embodiment of the invention, there are ten (10) sets of said apertures.

Figure 6:
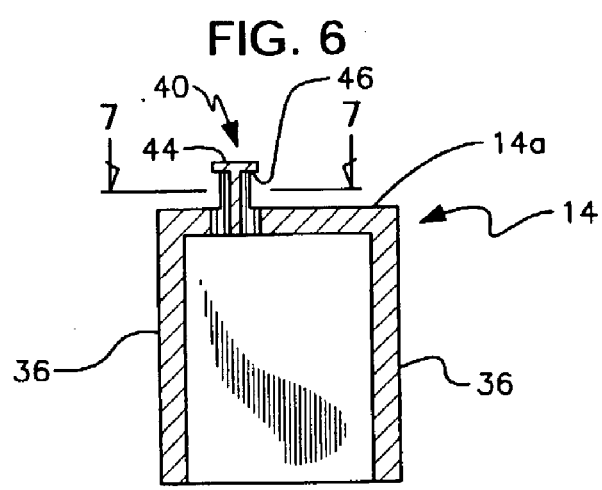
FIG. 6 is a sectional view taken along line 6—6 in FIG. 5.

A mounting post 40, depicted in FIGS. 4 and 6, is associated with each set of apertures so that in said commercial embodiment there are ten (10) of said mounting posts. Each mounting post 40 is centered with respect to its associated set of apertures, each mounting post is fluted, and each mounting post depends from lower flat surface 14a of working quadrant 14 as best understood from FIG. 4.

More particularly, each mounting post 40 has four semicircular flutes, collectively denoted 42 in FIG. 7, each of which is in registration with an associated aperture and the depth of each flute is substantially equal to the radius of its associated aperture. In this way, no part of a mounting post 40 occludes any of its four associated apertures as clearly depicted in said FIG. 7.

Flutes 42 extend from flat lower surface 14a to a point about two-thirds of the extent of each mounting post. Accordingly, about the lower third of each mounting post is not fluted, thereby forming a disc-shaped head 44 at the bottom of each mounting post. Thus, there is an undercut 46 formed in each mounting post 40 where a flute 42 meets head 44.

In the commercial embodiment where each set of apertures 38 has four apertures 38a, 38b, 38c, and 38d, and where each mounting post 40 has four flutes 42, the number of undercuts 46 in each mounting post is four. The number of apertures and hence the number of flutes and hence the number of undercuts may be increased or decreased. Four (4) is merely considered to be an optimal number but other numbers of apertures per set of apertures and hence other numbers of flutes and undercuts are within the scope of this invention.

This arrangement of sets of apertures 38 where each set of apertures has a mounting post 40 associated with it and where each mounting post is fluted as described and surmounted by an unfluted, disc-shaped head 44 to create a plurality of undercuts 46 is provided to hold the cast teeth 26 and associated gums that depend from lower flat surface 14a of opposing quadrant 14. The dental stone used to make the gums and teeth fills the apertures and the flutes. The respective heads 44 of the mounting posts 40 support the dental stone because the mounting posts depend from said flat lower surface.

FIGS. 8A, 8B, and 8C depict a third embodiment where a working base 50 has the same structure as working quadrant 12 but is semicircular in configuration. As such, it represents a full lower set of teeth and not just a quadrant as in the first two embodiments. Opposing top member 52 also has the same structure as opposing quadrant 14 in all respects except that said opposing top member is semicircular and represents a full set of upper teeth and not just a quadrant as in the first two embodiments. The same reference numerals are used in view of the common structure of the three embodiments.

The novel structure thus removes much of the guesswork associated with prior art techniques. Thus, the level of skill required to make a good set of model teeth is substantially reduced. Much less time is required as well. A lab equipped with the novel system will also become known for its consistency and reliability. Moreover, patient complaints about ill-fitting crowns and dentures will diminish.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A model and die system, comprising:
    a working base having a flat upper surface;
    a first row of bores formed in said flat upper surface in closely spaced relation to a preselected edge of said working base;
    a second row of bores formed in said working base in parallel relation to said first row of bores, said first row of bores being spaced between said second row of bores and said preselected edge of said working base;
    at least one cast tooth adapted to releasably engage said working base;
    said at least one cast tooth having a first pin and a second pin depending therefrom;
    said first pin disposed within a preselected bore of said first row of bores and said second pin disposed within a preselected bore of said second row of bores;
    said at least one cast tooth positioned so that a leading surface of said at least one cast tooth is substantially flush with said preselected edge of said working base;
    an opposing top member having a flat lower surface;
    a plurality of mounting posts depending from said opposing top member;
    a cast tooth being mounted on each mounting post of said plurality of mounting posts;
    a plurality of sets of apertures formed in said flat lower surface, said plurality of sets of apertures being positioned in a single row of sets of apertures;
    each set of apertures including a plurality of apertures arranged in circumferentially spaced apart relation to one another;
    each of said mounting posts being fluted;
    a fluted mounting post associated with each set of apertures;
    each fluted mounting post being centered with respect to its associated set of apertures;
    each fluted mounting post depending from said flat lower surface of said opposing top member;
    each fluted post having four semicircular flutes, each of which is in registration with an associated aperture of said sets of apertures;
    each flute having a depth substantially equal to the radius of its associated aperture so that no part of the mounting post occludes any of its four associated apertures;
    interconnecting means for interconnecting said working base and said opposing top member;
    whereby a bite between said at least one cast tooth mounted to said working base and said at least one cast tooth mounted to said opposing top member is checked by bringing said opposing top member toward said working base until said cast teeth abut one another, said interconnecting means serving to maintain alignment between said working base and said opposing top member as said opposing top member is brought into registration with said working base.

2. The system of claim 1, further comprising:
    each flute depending from said flat lower surface to a point about two-thirds of the extent of each mounting post so that about the lower third of each mounting post is not fluted, thereby forming a disc-shaped head at the bottom of each mounting post and further forming an undercut in each mounting post where a flute meets the disc-shaped head;
    each undercut holding part of a cast tooth depending from the lower flat surface of said opposing top member;
    whereby dental stone used to make cast gums and teeth fills the apertures and the flutes;
    whereby the respective disc-shaped heads of the mounting posts support the dental stone because the mounting posts depend from said flat lower surface.

3. The system of claim 1, further comprising:
    a thin foil disposed in overlying relation to said flat upper surface to cover said first and second row of bores, said foil being punctureable by said first and second pins.

4. The system of claim 1, wherein said means for interconnecting said working base and said opposing top member includes:
    a pair of upstanding guideposts mounted to opposite ends of said working base;
    a pair of guidepost-receiving apertures formed in opposite ends of said opposing top member;
    each guidepost of said pair of guideposts being slideably received within respective apertures of said pair of guidepost-receiving apertures.

5. The system of claim 1, wherein said means for interconnecting said working base and said opposing top includes a hinge means, said hinge means having a first part secured to an end wall of said working base and having a second part secured to an end wall of said opposing top member.

6. The system of claim 5, further comprising:
    an adjustment rod snugly and slideably received within said opposing top member;
    said adjustment rod having a flat free end that abuts said flat upper surface when said working base and said opposing top are in optimal juxtaposition with one another.

7. The model and die system of claim 1, further comprising:
    said working base having a generally straight, parallelepiped configuration that forms a working quadrant and said opposing top member having a generally straight, parallelepiped configuration that forms an opposing quadrant.

8. The model and die system of claim 7, further comprising:
    said working quadrant including said flat upper surface, a first and a second longitudinally extending sidewall, a first and a second transversely extending end wall, and an open bottom.

9. The system of claim 8, further comprising:
    said flat upper surface, said first and second longitudinally-extending sidewalls, said transversely-extending end walls and said open bottom wall defining a cavity that is partially filled by a material within which is formed said bores of said first and second rows of bores.

10. The system of claim 1, further comprising:
said opposing top member having a generally parallelepiped construction including said flat lower surface, a first and a second longitudinally extending sidewall, a first and a second transversely extending end wall, and an open top.

11. The model and die system of claim 1, further comprising:
said working base having a semicircular configuration and said opposing top member having a semicircular configuration.

12. A model and die system, comprising:
A working base having a flat upper surface;
an opposing top member having a flat lower surface;
a first row of bores formed in said flat upper surface in closely spaced relation to a preselected edge of said working base;
a second row of bores formed in said working base in parallel relation to said first row of bores, said first row of bores being spaced between said second row of bores and said preselected edge of said working base;
a cast tooth adapted to releasably engage said working base;
said cast tooth having a first pin and a second pin depending therefrom;
said first pin disposed within a preselected bore of said first row of bores and said secondd pin disposed within a preselected bore of said second row of bores;
said cast tooth positioned so that a leading surface of said cast tooth is substantially flush with said preselected edge of said working base;
a plurality of apertures formed in said flat lower surface of said opposing top member;
a plurality of mounting posts depending from said flat lower surface;
each aperture of said plurality of apertures adapted to receive and engage a one of said mounting posts;
a head formed in a lowermost end of each mounting post, each head having a diameter greater than a diameter of its mounting post;
a cast tooth being mounted on each mounting post, said head on each mounting post serving to support the cast tooth;
interconnecting means for interconnecting said working base and said opposing top member;
whereby a bite between said at least one cast tooth mounted to said working base and said at least one cast tooth mounted to said opposing top member is checked by bringing said opposing top member toward said working base until said cast teeth abut one another, said interconnecting means serving to maintain alignment between said working base and said opposing top member as said opposing top member is brought into registration with said working base.

\* \* \* \* \*